(12) United States Patent
Shariati (10) Patent No.: US 9,480,546 B2
(45) Date of Patent: Nov. 1, 2016

(54) HYSTEROPEXY MESH APPARATUSES AND METHODS

(71) Applicant: COLOPLAST A/S, Humlebaek (DK)

(72) Inventor: Amir Shariati, Parkland, FL (US)

(73) Assignee: Coloplast A/S, Humlebaek (DK)

( * ) Notice: Subject to any disclaimer, the term of this patent is extended or adjusted under 35 U.S.C. 154(b) by 192 days.

(21) Appl. No.: 14/449,459

(22) Filed: Aug. 1, 2014

(65) Prior Publication Data

US 2015/0038780 A1 Feb. 5, 2015

Related U.S. Application Data

(60) Provisional application No. 61/862,386, filed on Aug. 5, 2013.

(51) Int. Cl.
*A61F 2/00* (2006.01)
*A61B 17/42* (2006.01)

(52) U.S. Cl.
CPC ............ *A61F 2/0063* (2013.01); *A61F 2/0045* (2013.01); *A61B 17/4241* (2013.01); *A61F 2230/0019* (2013.01); *A61F 2230/0043* (2013.01)

(58) Field of Classification Search
CPC .............. A61F 2/0063; A61F 2/0045; A61F 2230/0043; A61F 2230/0019; A61B 17/4241
See application file for complete search history.

(56) References Cited

U.S. PATENT DOCUMENTS

| | | |
|---|---|---|
| 2,738,790 A | 3/1956 | Todt et al. |
| 4,009,711 A | 3/1977 | Uson |
| 5,230,694 A | 7/1993 | Rosenblum |
| 5,284,141 A | 2/1994 | Eibling |
| 5,356,432 A | 10/1994 | Rutkow et al. |
| 5,899,909 A | 5/1999 | Claren et al. |
| 5,934,283 A | 8/1999 | Willem et al. |
| 6,042,534 A | 3/2000 | Gellman et al. |
| 6,050,937 A | 4/2000 | Benderev |
| 6,102,886 A | 8/2000 | Lundquist et al. |
| 6,197,036 B1 | 3/2001 | Tripp et al. |
| 6,200,330 B1 | 3/2001 | Benderev et al. |
| 6,273,852 B1 | 8/2001 | Lehe et al. |
| 6,302,840 B1 | 10/2001 | Benderev |
| 6,328,686 B1 | 12/2001 | Kovac |
| 6,355,065 B1 | 3/2002 | Gabbay |
| 6,406,420 B1 | 6/2002 | McCarthy et al. |
| 6,491,703 B1 | 12/2002 | Ulmsten |

(Continued)

FOREIGN PATENT DOCUMENTS

| | | |
|---|---|---|
| AU | 2002241673 | 8/2002 |
| EP | 1484022 A2 | 12/2004 |

(Continued)

OTHER PUBLICATIONS

Chon, J.; D. Bodell; K. Kobashi; G. Leach, Results of the Transvaginal Cadaveric Prolapse Repair with Sling (CAP); p. 150, 2002.

(Continued)

*Primary Examiner* — Christine H Matthews
*Assistant Examiner* — Joshua D Lannu
(74) *Attorney, Agent, or Firm* — Coloplast Corp., Coloplast A/S; Nick Baumann (57) ABSTRACT

The invention describes embodiments of apparatuses and methods of using a hysteropexy mesh.

3 Claims, 5 Drawing Sheets

(56) References Cited

U.S. PATENT DOCUMENTS

| | | | |
|---|---|---|---|
| 6,502,578 B2 | 1/2003 | Raz et al. | |
| 6,592,515 B2 | 7/2003 | Thierfelder et al. | |
| 6,599,318 B1 | 7/2003 | Gabbay | |
| 6,638,211 B2 | 10/2003 | Suslian et al. | |
| 6,666,817 B2 | 12/2003 | Li | |
| 6,685,626 B2 | 2/2004 | Wironen | |
| 6,695,855 B1 | 2/2004 | Gaston | |
| 6,808,486 B1 | 10/2004 | O'Donnell | |
| 6,884,212 B2 | 4/2005 | Thierfelder et al. | |
| 6,953,428 B2 | 10/2005 | Gellman et al. | |
| 7,025,063 B2 | 4/2006 | Snitkin et al. | |
| 7,083,568 B2 | 8/2006 | Neisz et al. | |
| 7,083,637 B1 | 8/2006 | Tannhauser | |
| 7,131,943 B2 | 11/2006 | Kammerer | |
| 7,175,591 B2 | 2/2007 | Kaladelfos | |
| 7,204,802 B2 | 4/2007 | De Laval | |
| 7,393,319 B2 | 7/2008 | Merade et al. | |
| 7,431,690 B2 | 10/2008 | Merade et al. | |
| 7,517,313 B2 | 4/2009 | Thierfelder et al. | |
| 7,527,588 B2 | 5/2009 | Zaddem et al. | |
| 7,556,598 B2 | 7/2009 | Rao | |
| 7,559,885 B2 | 7/2009 | Merade et al. | |
| 7,878,969 B2 | 2/2011 | Chu et al. | |
| 7,901,346 B2 | 3/2011 | Kovac et al. | |
| 8,029,435 B2 | 10/2011 | Merade et al. | |
| 8,057,382 B2 | 11/2011 | Thierfelder et al. | |
| 8,109,867 B2 | 2/2012 | Rosenblatt | |
| 8,128,554 B2 | 3/2012 | Browning | |
| 8,147,478 B2 | 4/2012 | Snitkin et al. | |
| 8,182,412 B2 | 5/2012 | Browning | |
| 8,182,413 B2 | 5/2012 | Browning | |
| 8,469,877 B2 | 6/2013 | Browning | |
| 8,834,348 B2 | 9/2014 | Crabb | |
| 2001/0031973 A1 | 10/2001 | Nobles et al. | |
| 2002/0028980 A1 | 3/2002 | Thierfelder et al. | |
| 2002/0072694 A1 | 6/2002 | Snitkin et al. | |
| 2002/0099260 A1 | 7/2002 | Suslian et al. | |
| 2002/0128670 A1 | 9/2002 | Ulmsten et al. | |
| 2002/0161382 A1 | 10/2002 | Neisz et al. | |
| 2002/0188169 A1 | 12/2002 | Kammerer et al. | |
| 2003/0023137 A1 | 1/2003 | Gellman | |
| 2003/0023138 A1 | 1/2003 | Luscombe | |
| 2003/0045774 A1 | 3/2003 | Staskin et al. | |
| 2003/0078471 A1 | 4/2003 | Foley et al. | |
| 2003/0130670 A1 | 7/2003 | Anderson et al. | |
| 2003/0130745 A1 | 7/2003 | Cherok et al. | |
| 2003/0171644 A1 | 9/2003 | Anderson et al. | |
| 2003/0176762 A1 | 9/2003 | Kammerer | |
| 2003/0195386 A1 | 10/2003 | Thierfelder et al. | |
| 2003/0212305 A1 | 11/2003 | Anderson et al. | |
| 2003/0216814 A1 | 11/2003 | Siegel et al. | |
| 2003/0220538 A1 | 11/2003 | Jacquetin et al. | |
| 2004/0002734 A1 | 1/2004 | Fallin et al. | |
| 2004/0039453 A1 | 2/2004 | Anderson et al. | |
| 2004/0054253 A1 | 3/2004 | Snitkin et al. | |
| 2004/0087970 A1 | 5/2004 | Chu et al. | |
| 2004/0138706 A1 | 7/2004 | Abrams et al. | |
| 2004/0143152 A1 | 7/2004 | Grocela et al. | |
| 2004/0230092 A1 | 11/2004 | Thierfelder et al. | |
| 2004/0231678 A1 | 11/2004 | Fierro | |
| 2004/0249240 A1 | 12/2004 | Goldmann et al. | |
| 2004/0249473 A1 | 12/2004 | Delorme et al. | |
| 2005/0004576 A1 | 1/2005 | Benderev | |
| 2005/0027160 A1 | 2/2005 | Siegel et al. | |
| 2005/0085688 A1 | 4/2005 | Girard et al. | |
| 2005/0101834 A1 | 5/2005 | Merade | |
| 2005/0240076 A1 | 10/2005 | Neisz et al. | |
| 2005/0283040 A1 | 12/2005 | Greenhalgh | |
| 2006/0004246 A1 | 1/2006 | Selikowitz | |
| 2006/0058575 A1 | 3/2006 | Zaddem et al. | |
| 2006/0089525 A1 | 4/2006 | Mamo et al. | |
| 2006/0122457 A1 | 6/2006 | Kovac et al. | |
| 2006/0130848 A1 | 6/2006 | Carey | |
| 2006/0134159 A1 | 6/2006 | Nicita | |
| 2006/0205995 A1 | 9/2006 | Browning | |
| 2006/0229596 A1 | 10/2006 | Weiser et al. | |
| 2006/0247490 A1 | 11/2006 | Merade et al. | |
| 2006/0264698 A1 | 11/2006 | Kondonis et al. | |
| 2006/0287571 A1 | 12/2006 | Gozzi et al. | |
| 2007/0021649 A1 | 1/2007 | Nowlin et al. | |
| 2007/0032695 A1 | 2/2007 | Weiser | |
| 2007/0049791 A1 | 3/2007 | Merade et al. | |
| 2007/0055095 A1 | 3/2007 | Chu et al. | |
| 2007/0161849 A1* | 7/2007 | Goldberg | A61F 2/0045 600/30 |
| 2007/0225546 A1 | 9/2007 | Anderson et al. | |
| 2007/0270890 A1 | 11/2007 | Miller | |
| 2007/0293717 A1 | 12/2007 | Kaleta et al. | |
| 2008/0009665 A1 | 1/2008 | Merade et al. | |
| 2008/0021265 A1* | 1/2008 | Garbin | A61B 17/06109 600/30 |
| 2008/0076963 A1 | 3/2008 | Goria | |
| 2008/0132754 A1 | 6/2008 | Thierfelder et al. | |
| 2008/0140218 A1 | 6/2008 | Staskin et al. | |
| 2008/0177132 A1 | 7/2008 | Alinsod et al. | |
| 2008/0196729 A1 | 8/2008 | Browning | |
| 2008/0210247 A1 | 9/2008 | De Leval | |
| 2008/0287956 A1 | 11/2008 | Smith et al. | |
| 2008/0287968 A1 | 11/2008 | Smith et al. | |
| 2008/0300607 A1 | 12/2008 | Meade et al. | |
| 2009/0005867 A1 | 1/2009 | Lefranc et al. | |
| 2009/0012351 A1 | 1/2009 | Anderson et al. | |
| 2009/0048479 A1 | 2/2009 | Goria | |
| 2009/0137862 A1 | 5/2009 | Evans et al. | |
| 2009/0171142 A1 | 7/2009 | Chu | |
| 2009/0171377 A1 | 7/2009 | Intoccia et al. | |
| 2009/0216072 A1 | 8/2009 | Zipper | |
| 2009/0247816 A1 | 10/2009 | Merade et al. | |
| 2010/0130814 A1 | 5/2010 | Dubernard | |
| 2010/0191038 A1 | 7/2010 | Kubalak et al. | |
| 2010/0197998 A1 | 8/2010 | Comiter et al. | |
| 2010/0197999 A1 | 8/2010 | Deegan et al. | |
| 2010/0198004 A1 | 8/2010 | Moschel et al. | |
| 2010/0261954 A1* | 10/2010 | Townsend | A61F 2/0045 600/37 |
| 2010/0261956 A1 | 10/2010 | Townsend et al. | |
| 2010/0305394 A1 | 12/2010 | Rosenblatt | |
| 2011/0022061 A1 | 1/2011 | Orphanos et al. | |
| 2011/0125289 A1 | 5/2011 | Armstrong et al. | |
| 2011/0237878 A1 | 9/2011 | Browning | |
| 2011/0263930 A1 | 10/2011 | Rapp | |
| 2012/0022317 A1 | 1/2012 | Merade et al. | |
| 2012/0022318 A1 | 1/2012 | Thierfelder et al. | |
| 2012/0108894 A1 | 5/2012 | Young et al. | |
| 2012/0149974 A1 | 6/2012 | Comiter et al. | |
| 2012/0165603 A1 | 6/2012 | Comiter et al. | |
| 2012/0259169 A1 | 10/2012 | Merade et al. | |
| 2013/0046132 A1 | 2/2013 | Buie et al. | |
| 2013/0046133 A1 | 2/2013 | Buie et al. | |
| 2013/0066145 A1 | 3/2013 | Fairneny et al. | |
| 2013/0231524 A1 | 9/2013 | Merade et al. | |
| 2014/0039244 A1 | 2/2014 | Browning | |
| 2014/0039248 A1 | 2/2014 | Browning | |
| 2014/0051917 A1 | 2/2014 | Browning | |
| 2014/0194675 A1 | 7/2014 | Merade et al. | |
| 2014/0194676 A1 | 7/2014 | Comiter et al. | |

FOREIGN PATENT DOCUMENTS

| | | |
|---|---|---|
| EP | 2002800 A1 | 12/2008 |
| EP | 2754412 | 7/2014 |
| FR | 2973217 A1 | 10/2012 |
| FR | 2976788 | 12/2012 |
| JP | 2004522470 T2 | 7/2004 |
| JP | 2004525483 T2 | 8/2004 |
| RU | 2185779 C2 | 7/2002 |
| RU | 2243729 C1 | 1/2005 |
| RU | 2275883 C2 | 5/2006 |
| WO | 03002027 A1 | 1/2003 |
| WO | 03075792 A1 | 9/2003 |
| WO | 03094784 A2 | 11/2003 |
| WO | 03096929 A1 | 11/2003 |
| WO | 2004012579 A2 | 2/2004 |
| WO | 2004012626 A1 | 2/2004 |

(56) References Cited

FOREIGN PATENT DOCUMENTS

| WO | 2004017845 A1 | 3/2004 |
|---|---|---|
| WO | 2004017862 A2 | 3/2004 |
| WO | 2004045457 A1 | 6/2004 |
| WO | 2004091442 A2 | 10/2004 |
| WO | 2005027786 A1 | 3/2005 |
| WO | 2005110243 A2 | 11/2005 |
| WO | 2006020530 A2 | 2/2006 |
| WO | 2006034719 A1 | 4/2006 |
| WO | 2006041861 A2 | 4/2006 |
| WO | 2006045042 A1 | 4/2006 |
| WO | 2007049154 A1 | 5/2007 |
| WO | 2007059199 A2 | 5/2007 |
| WO | WO 2007/066169 | 6/2007 |
| WO | 2007118260 A1 | 10/2007 |
| WO | 2007137226 A2 | 11/2007 |
| WO | 2007149555 A2 | 12/2007 |
| WO | 2008152435 A1 | 12/2008 |
| WO | 2010087923 | 8/2010 |
| WO | 2010093421 A2 | 8/2010 |
| WO | 2011037837 A2 | 3/2011 |
| WO | 2011082350 A1 | 7/2011 |
| WO | 2011106419 A1 | 9/2011 |
| WO | 2012054985 A1 | 5/2012 |

OTHER PUBLICATIONS

Kobashi, K; S.Mee; G. Leach; A New Technique for Cystocele Repair and Transvaginal Sling: The Cadaverix Prolaps Repair and Sling (CaPS); Elsevier Science Inc.; Dec. 2000; pp. 9-14.

Kobashi, K. and Govier, F.; The Use of Solvent-Dehydrated Cadaveric Fascia Lata (TUTOPLAST) in Slings and Cystocele Repairs; the Virginia Mason Experience; Virginia Mason Medical Center; J. Urol 2002; p. 151.

Almeida, Silvio H.M. et al; Use of Cadaveric Fascia Lata to Correct Grade IV Cystocele; Official Journal of the Brazilian Society of Urology, State University of Londrian, Parana, Brazil; pp. 48-52, Feb. 2003.

Moir, The Journal of Obstetrics and Gyneacolog, Jan. 1968.

Shaw, British Medical Journal, Jun. 1949.

Ulmsten et al, International Urogynecology Journal, vol. 7, 1996.

* cited by examiner

HYSTEROPEXY MESH APPARATUSES AND METHODS

CROSS-REFERENCE TO RELATED APPLICATIONS

This application claims the benefit of Provisional Application Ser. No. 61/862,386, filed Aug. 5, 2013, the contents of which are incorporated herein in their entirety for all purposes.

FIELD OF THE INVENTION

The invention relates generally to apparatuses and methods for performing hysteropexy.

BACKGROUND OF THE INVENTION

Uterine prolapse occurs when pelvic floor muscles and ligaments stretch and weaken, providing inadequate support for the uterus. The uterus then descends into or protrudes from the vagina. Uterine prolapse can happen to women of any age, but it often affects postmenopausal women who've had one or more vaginal deliveries. Damage to supportive tissues during pregnancy and childbirth, effects of gravity, loss of estrogen, and repeated straining over the years all can weaken the pelvic floor and lead to uterine prolapse.

At the present time, sacral colpopexy is the gold standard procedure for post-hysterectomy patients who have vaginal vault prolapse. Patients who still have their uterus and are undergoing sacral colpopexy are having a total hysterectomy or a supracervical hysterectomy at the same time. This can lead to mesh erosion. The only reason that most hysterectomies are performed is because the appropriate mesh that can provide anterior, posterior, and apical uterine support is not available. Hysteropexy is the surgical fixation of a displaced uterus. The hysteropexies that are performed at the present time are either supporting the uterus by placing the mesh anteriorly or posteriorly.

BRIEF SUMMARY OF THE INVENTION

The present invention provides embodiments of apparatuses and methods configured for use in hysteropexy and methods of using the same.

In one embodiment, a hysteropexy is presented comprising a hysteropexy mesh comprising: an anterior vaginal portion, substantially rectangular in shape, having a major dimension of about 10 cm and a minor dimension of about 4.0 cm; a right broad ligament portion, substantially L-shaped, extending from one long edge of the anterior vaginal portion and having a thickness dimension about 1.2 cm and a major dimension of about 3.5 cm; a left broad ligament portion, substantially L-shaped, extending from the other long edge of the anterior vaginal portion and having a thickness dimension about 1.2 cm and a major dimension of about 3.5 cm; a sacral portion, substantially rectangular in shape, having a major dimension of about 8.0 cm and a minor dimension of about 4.0 cm; and a posterior vaginal portion, substantially rectangular in shape, having a major dimension of about 15 cm and a minor dimension of about 4.0 cm; where the left broad ligament portion extends between and connects the anterior vaginal portion and the posterior vaginal portion.

In another embodiment the hysteropexy mesh comprises one of polypropylene, polyester, polyethylene, silicone, a urethane, a polyurethane, copolymers, or block copolymers thereof.

In another embodiment a method of treating hysteropexy is provided comprising: create a peritoneal incision just above the rectum; separate rectum from the posterior aspect of the vagina by dissection until the perineal body is reached and the levator muscles are exposed; penetrate peritoneum overlying the sacral promontory and inferiorly dissected to meet posterior dissection from cul de sac; identify and clear off anterior longitudinal ligament and presacral vessels on the sacral promontory; manipulate uterus to create vesi-couterine fascia incision and bladder flap; dissect vesico-vaginal space to separate the bladder from the anterior aspect of the vagina until the level of the trigone is reached; create broad ligament incisions on each side near the cervix; insert hysteropexy mesh and attach by suture the posterior vaginal portion of the mesh to the posterior aspect of the vagina; pass folded anterior vaginal portion and right and left broad ligament arms through incision in the broad ligament on the left; unfold anterior vaginal portion and attach by suture to the anterior aspect of the vagina; pass right broad ligament portion through incision in the broad ligament on the right; manipulator uterus and attach right broad ligament portion of mesh to posterior vaginal portion of mesh and the posterior aspect of the cervix; attach sacral portion of mesh to the anterior longitudinal ligament at the level of the S1 vertebrae by suture in a tension free fashion; close peritoneal incision made on the sacrum by suture and cover with the bladder peritoneum using another suture; and close any remaining incisions to complete procedure.

In another embodiment the hysteropexy procedure is performed robotically, laparoscopically, or in open surgery through a laparotomy incision.

In yet another embodiment a medical device kit is provided comprising the hysteropexy mesh of the current disclosure and instructions for implantation.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Embodiments and methods for using a hysteropexy mesh configured to be implanted in the pelvic region of a patient are discussed below.

Figure 1:
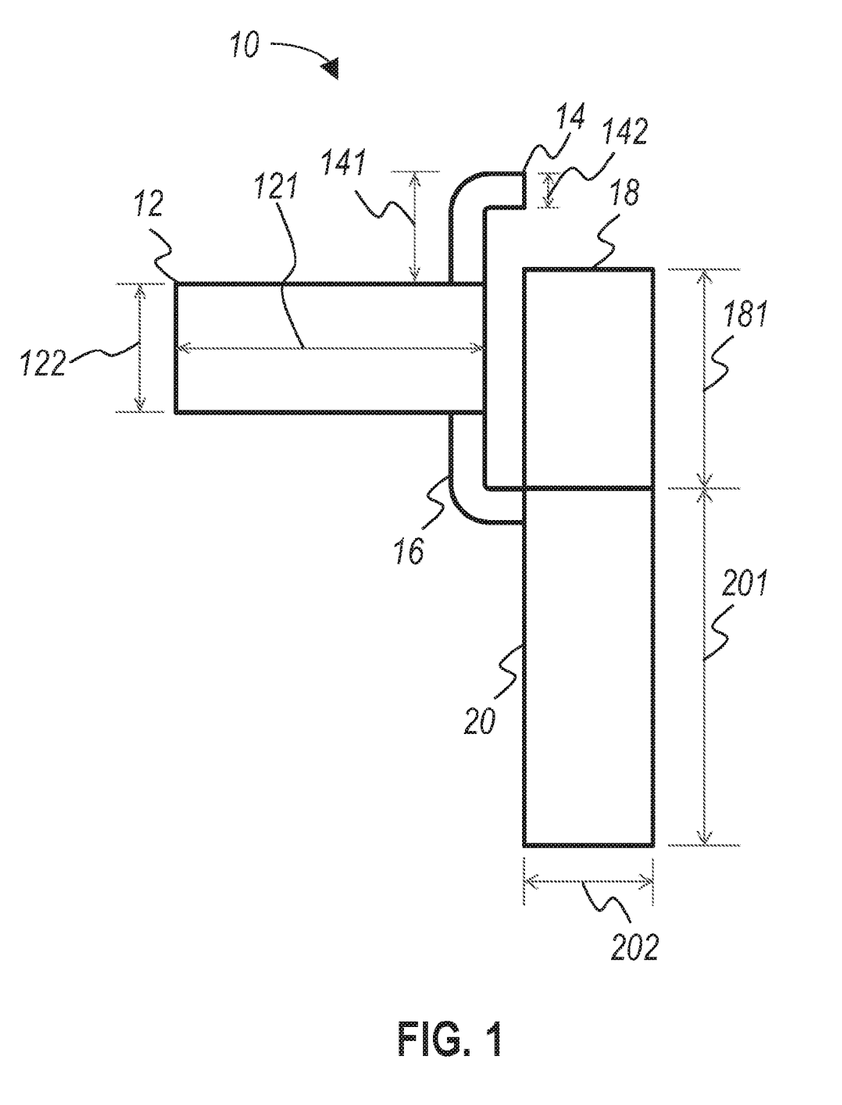
FIG. 1 is a plan view of an embodiment of a hysteropexy mesh comprising an anterior vaginal portion, a right broad ligament portion, a left broad ligament portion, a sacral portion, and a posterior vaginal portion.

A plan view of an embodiment of a hysteropexy mesh 10 is shown in FIG. 1. Mesh 10 comprises an anterior vaginal portion 12, a right broad ligament portion 14, a left broad ligament portion 16, a sacral portion 18, and a posterior vaginal portion 20.

In the illustrated embodiment, mesh 10 is an integral mesh, and each of the above-identified portions 12-20 are regions of the whole. In such embodiments, mesh 10 may be cut, stamped, or otherwise machined from a single sheet of mesh.

In other embodiments, the portions may be separate or separable. For example, in certain embodiments, anterior vaginal portion 12, right broad ligament portion 14, and left broad ligament portion 16 may comprise one integral mesh, sacral portion 18 may comprise a second integral mesh, and posterior vaginal portion 20 may comprise a third integral mesh, and these may be coupled to each other, such as a with a suture or an ultrasonic weld.

In the illustrated embodiment, anterior vaginal portion 12 is substantially rectangular in shape with a major dimension 121 of about 10 cm and a minor dimension 122 of about 4.0 cm.

Right broad ligament portion 14 extends from the long edge of anterior vaginal portion 12, such that an edge of right broad ligament portion 14 is in common (i.e., substantially aligned) with a short edge of anterior vaginal portion 12.

Left broad ligament portion 16 extends from the other long edge of anterior vaginal portion 12, such that an edge of left broad ligament portion 16 is in common (i.e., substantially aligned) with the same short edge of anterior vaginal portion 12 and the edge of right broad ligament portion 14.

Right and left broad ligament portions 14 and 16 are substantially L-shaped, and may be rounded as shown in FIG. 1. Each of the broad ligament portions has a thickness dimension 142 of about 1.2 cm and a major dimension 141 of about 3.5 cm.

Left broad ligament portion 16 is between anterior vaginal portion 12 and posterior vaginal portion 20. Posterior vaginal portion 20 is substantially rectangular in shape and has a major dimension 201 of about 15 cm and a minor dimension 202 of about 4.0 cm. The edge of left broad ligament portion 16 that is in common with the edge of anterior vaginal portion 12 and the edge of right broad ligament portion 14 is also in common with a short edge of posterior vaginal portion 20.

Sacral portion 18 is substantially rectangular in shape and has a major dimension 181 of about 8 cm and a minor dimension 202 of about 4.0 cm.

Figure 2:
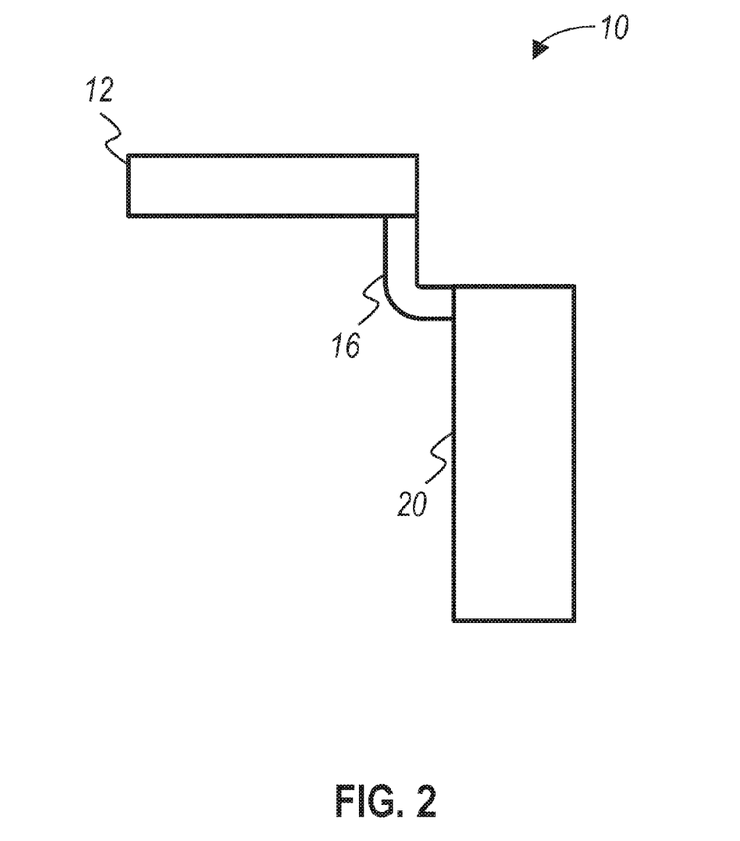
FIG. 2 is a plan view of an embodiment of a hysteropexy mesh with anterior vaginal portion folded along its longitudinal midline.

As shown in FIG. 2, mesh 10 is configured to be folded substantially along the longitudinal midline of anterior vaginal portion 12 and is further configured to be folded between sacral portion 18 and posterior vaginal portion 20. In certain embodiments, mesh 10 is packaged as depicted in FIG. 2, such that mesh 10 is folded substantially along the longitudinal midline of anterior vaginal portion 12 and between sacral portion 18 and posterior vaginal portion 20. In such embodiments, mesh 10 may be removed from the packaging, passed through the left side broad ligament incision, then unfolded to be attached to the anterior vaginal wall.

Figure 3:
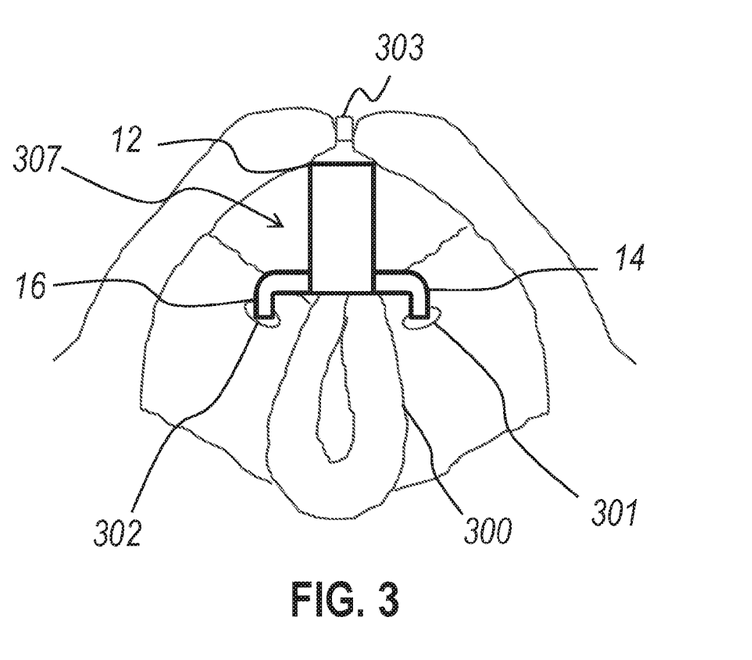
FIG. 3 is an anterior view of an embodiment of a hysteropexy mesh implanted in the pelvic region showing the uterus, the pubic bone, and the anterior vagina.
Figure 4:
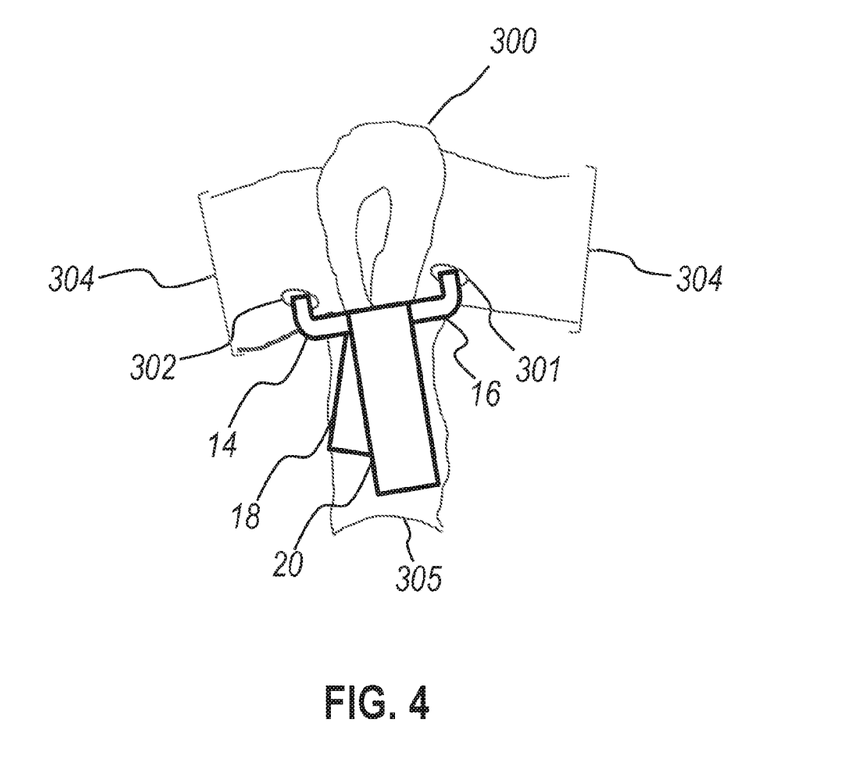
FIG. 4 is a posterior view of an embodiment of a hysteropexy mesh implanted in the pelvic region showing the uterus, the broad ligament, and a portion of the sacrum.
Figure 5:
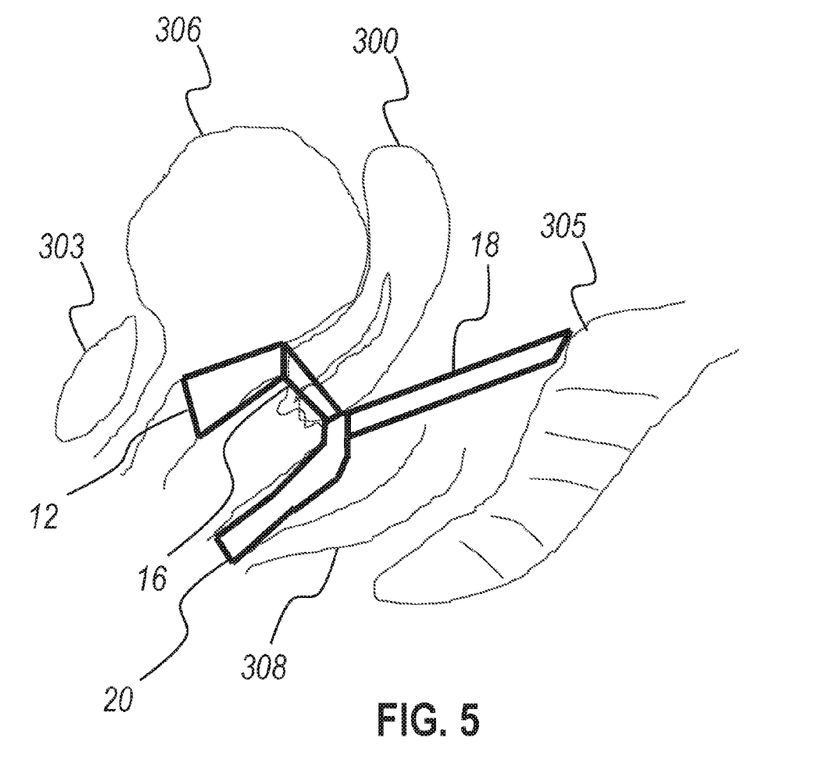
FIG. 5 is a lateral view of an embodiment of a hysteropexy mesh implanted in the pelvic region showing the pubic bone, the bladder, the uterus, the rectum, and the sacrum.

FIGS. 3-5 are anterior, posterior, and lateral illustrations, respectively, of mesh 10 implanted into the pelvic region of a patient. FIG. 3 is an anterior view of mesh 10 implanted in the pelvic region showing the uterus 300, the pubic bone 303, and the anterior vagina 307. FIG. 4 is a posterior view of mesh 10 implanted in the pelvic region showing uterus 300, the broad ligament 304, and a portion of the sacrum 305. FIG. 5 is a lateral view of mesh 10 implanted in the pelvic region showing pubic bone 303, bladder 306, uterus 300, rectum 308, and sacrum 305. These figures may be reference to better understand the steps of embodiments of the method discussed below.

In one embodiment, the mesh 10 is a knitted monofilament polypropylene mesh having a mass per area between approximately 15-35 g/m$^2$ with a pore size between approximately 500-1500 μm and a thickness of approximately 260 μm. This mesh is thin and light weight (i.e., the basis weight is less than approximately 35 g/m$^2$) to provide a thin and comfortable mesh that is less likely to erode tissue that contacts the mesh and less likely to be sensed through the tissue layers by the patient. Other suitable materials for the support include fabrics formed from polyester, polyethylene, silicone, urethanes, polyurethanes, copolymers, or block copolymers of these or suitably similar polymeric materials. Suitable such knitted monofilament polypropylene mesh is available from Coloplast Corp., Minneapolis, Minn. Other suitable woven polypropylene mesh material is available from, for example, HemiaMesh, Chivasso, Italy.

Embodiments of the disclosed method may be performed robotically, laparoscopically, or in open surgery through a laparotomy incision.

In embodiments where the method is performed robotically, a uterine manipulator may be placed vaginally to allow for manipulation of uterus 300 for the anterior and posterior dissection of the vaginal walls and attachment of the mesh. Then a robotic tenaculum may be used to grab the fundus of the uterus to manipulate the uterus for the anterior and posterior dissection of the vaginal walls and attachment of the mesh. A tenaculum can then be used through an accessory port to be placed on the fundus of the uterus to manipulate the uterus for the anterior and posterior dissection of the vaginal walls and attachment of the mesh.

In embodiments where the procedure is being performed laparoscopically, the tenaculum may be used to be placed on the fundus of uterus 300 to manipulate uterus 300 for the anterior and posterior dissection of the vaginal walls and attachment of the mesh or a uterine manipulator may be placed vaginally to allow for manipulation of uterus 300 for the anterior and posterior dissection of the vaginal walls and attachment of the mesh.

In embodiments where the procedure is being performed open through a laparotomy incision a uterine manipulator may be placed vaginally to allow for manipulation of uterus 300 for the anterior and posterior dissection of the vaginal walls and attachment of the mesh.

In the disclosed embodiments, the other steps of the method may be performed as follows.

Uterus 300 is elevated so the posterior vagina is visualized. An incision is made in the peritoneum just above the rectum 308. Dissection is then performed bluntly and sharply in the rectovaginal space to separate rectum 308 from the posterior aspect of the vagina until the perineal body is reached and the levator muscles are exposed.

After that, the peritoneum overlying the sacral promontory is tented up and entered sharply with scissors. The peritoneal dissection is then carried inferiorly to meet the dissection posteriorly in the cul de sac below. The anterior longitudinal ligament as well as the presacral vessels on the sacral promontory are identified and cleared off.

Uterus 300 is then pulled dorsally and apically so that the anterior aspect of uterus 300 and the vagina are visualized. An incision is made in the vesicouterine fascia and the bladder flap is created sharply. The dissection is performed bluntly and sharply in the vesicovaginal space to separate the bladder from the anterior aspect of the vagina. This is done until the level of the trigone is reached.

Two one-centimeter incisions 301, 302 are made with the use of scissors and/or cautery in the broad ligament on each side near the cervix.

Then, posterior vaginal portion 20 of mesh 10 is attached to the posterior aspect of the vagina, such as with interrupted sutures.

The folded anterior vaginal portion 12 and the right and left broad ligament arms 14, 16 are then passed through incision 301 in the broad ligament on the left .

Anterior vaginal portion 12 is then unfolded and attached to the anterior aspect of the vagina using interrupted sutures.

Right broad ligament portion 14 is then passed through incision 302 in the broad ligament on the right. Uterus 300 is then lifted again, such as with a tenaculum or a manipulator and right broad ligament portion 14 of mesh 10 is attached to posterior vaginal portion 20 of mesh 10 and the posterior aspect of the cervix.

Sacral portion 18 of mesh 10 is than attached to the anterior longitudinal ligament at the level of the S1 vertebrae, such as with two interrupted sutures in tension free fashion.

To minimize exposure of the mesh to intraperitoneal organs, posterior vaginal portion 20 of mesh 10 and the peritoneal incision made on the sacrum are than closed using absorbable suture. Anterior vaginal portion 12 of mesh 10 is then covered with the bladder peritoneum using another absorbable suture. Any remaining incisions are closed and the surgery is complete.

In the specification and in the claims, the terms "including" and "comprising" are open-ended terms and should be interpreted to mean "including, but not limited to . . . " These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The following paragraphs enumerated consecutively from 1 to 6 provide for various aspects of the present invention.

In one embodiment, in a first paragraph (1), the present invention provides a hysteropexy mesh comprising: an anterior vaginal portion, substantially rectangular in shape, having a major dimension of about 10 cm and a minor dimension of about 4.0 cm; a right broad ligament portion, substantially L-shaped, extending from one long edge of the anterior vaginal portion and having a thickness dimension about 1.2 cm and a major dimension of about 3.5 cm; a left broad ligament portion, substantially L-shaped, extending from the other long edge of the anterior vaginal portion and having a thickness dimension about 1.2 cm and a major dimension of about 3.5 cm; a sacral portion, substantially rectangular in shape, having a major dimension of about 8.0 cm and a minor dimension of about 4.0 cm; and a posterior vaginal portion, substantially rectangular in shape, having a major dimension of about 15 cm and a minor dimension of about 4.0 cm; where the left broad ligament portion extends between and connects the anterior vaginal portion and the posterior vaginal portion.

(2) The hysteropexy mesh of claim 1, wherein the mesh comprises one of polypropylene, polyester, polyethylene, silicone, a urethane, a polyurethane, copolymers, or block copolymers thereof.

(3) A method of treating hysteropexy comprising: create a peritoneal incision just above the rectum; separate rectum from the posterior aspect of the vagina by dissection until the perineal body is reached and the levator muscles are exposed; penetrate peritoneum overlying the sacral promontory and inferiorly dissected to meet posterior dissection from cul de sac; identify and clear off anterior longitudinal ligament and presacral vessels on the sacral promontory; manipulate uterus to create vesicouterine fascia incision and bladder flap; dissect vesicovaginal space to separate the bladder from the anterior aspect of the vagina until the level of the trigone is reached; create broad ligament incisions on each side near the cervix; insert hysteropexy mesh and attach by suture the posterior vaginal portion of the mesh to the posterior aspect of the vagina; pass folded anterior vaginal portion and right and left broad ligament arms through incision in the broad ligament on the left; unfold anterior vaginal portion and attach by suture to the anterior aspect of the vagina; pass right broad ligament portion through incision in the broad ligament on the right; manipulator uterus and attach right broad ligament portion of mesh to posterior vaginal portion of mesh and the posterior aspect of the cervix;

attach sacral portion of mesh to the anterior longitudinal ligament at the level of the S1 vertebrae by suture in a tension free fashion; close peritoneal incision made on the sacrum by suture and cover with the bladder peritoneum using another suture; and close any remaining incisions to complete procedure.

(4) The method of paragraph (3), wherein the procedure is performed robotically, laparoscopically, or in open surgery through a laparotomy incision.

(5) A medical device kit comprising: the hysteropexy mesh of paragraph (1); and instructions for the implantation of the medical device.

(6) The medical device kit of paragraph (5), wherein the instructions comprise: create a peritoneal incision just above the rectum; separate rectum from the posterior aspect of the vagina by dissection until the perineal body is reached and the levator muscles are exposed; penetrate peritoneum overlying the sacral promontory and inferiorly dissected to meet posterior dissection from cul de sac; identify and clear off anterior longitudinal ligament and presacral vessels on the sacral promontory; manipulate uterus to create vesicouterine fascia incision and bladder flap; dissect vesicovaginal space to separate the bladder from the anterior aspect of the vagina until the level of the trigone is reached; create broad ligament incisions on each side near the cervix; insert hysteropexy mesh and attach by suture the posterior vaginal portion of the mesh to the posterior aspect of the vagina; pass folded anterior vaginal portion and right and left broad ligament arms through incision in the broad ligament on the left; unfold anterior vaginal portion and attach by suture to the anterior aspect of the vagina; pass right broad ligament portion through incision in the broad ligament on the right; manipulator uterus and attach right broad ligament portion of mesh to posterior vaginal portion of mesh and the posterior aspect of the cervix; attach sacral portion of mesh to the anterior longitudinal ligament at the level of the S1 vertebrae by suture in a tension free fashion; close peritoneal incision made on the sacrum by suture and cover with the bladder peritoneum using another suture; and close any remaining incisions to complete procedure.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method of treating hysteropexy comprising:
creating a peritoneal incision just above a rectum;
separating the rectum from a posterior aspect of a vagina by dissection until a perineal body is reached and levator muscles are exposed;
penetrating a bladder peritoneum overlying a sacral promontory and inferiorly dissecting from a posterior cul de sac;
identifying and clearing off an anterior longitudinal ligament and presacral vessels on the sacral promontory;
manipulating a uterus to create a vesicouterine fascia incision and bladder flap;
dissecting vesicovaginal space to separate a bladder from an anterior aspect of the vagina until a level of a trigone is reached;
creating broad ligament incisions on each side near a cervix;
inserting a hysteropexy mesh and attaching by suture a posterior vaginal portion of the hysteropexy mesh to a posterior aspect of the vagina, the hysteropexy mesh further including
an anterior vaginal portion, substantially rectangular in shape, having a major dimension of about 10 cm and a minor dimension of about 4.0 cm;
a right broad ligament portion, substantially L-shaped, extending from one long edge of the anterior vaginal portion and having a thickness dimension about 1.2 cm and a major dimension of about 3.5 cm;
a left broad ligament portion, substantially L-shaped, extending from another long edge of the anterior vaginal portion and having a thickness dimension about 1.2 cm and a major dimension of about 3.5 cm;
a sacral portion, substantially rectangular in shape, having a major dimension of about 8.0 cm and a minor dimension of about 4.0 cm; and
the posterior vaginal portion, substantially rectangular in shape, having a major dimension of about 15 cm and a minor dimension of about 4.0 cm,
where the left broad ligament portion extends between and connects the anterior vaginal portion and the posterior vaginal portion;
passing the anterior vaginal portion of the hysteropexy mesh configured in a folded state and the right and the left broad ligament portions of the hysteropexy mesh through the broad ligament incision on a left;
unfolding the anterior vaginal portion of the hysteropexy mesh and attaching by suture to an anterior aspect of the vagina;
passing the right broad ligament portion of the hysteropexy mesh through the broad ligament incision on a right;
manipulating the uterus and attaching the right broad ligament portion of the hysteropexy mesh to the posterior vaginal portion of the hysteropexy mesh and a posterior aspect of the cervix;
attaching the sacral portion of the hysteropexy mesh to an anterior longitudinal ligament at a level of an S1 vertebrae by suture in a tension free fashion;
closing a peritoneal incision made on a sacrum by suture and cover with the bladder peritoneum using another suture; and
closing incisions to complete the method.

2. The method of claim 1, wherein the method is performed robotically, laparoscopically, or in open surgery through a laparotomy incision.

3. A medical device kit comprising:
a hysteropexy mesh, the hysteropexy mesh further including
an anterior vaginal portion, substantially rectangular in shape, having a major dimension of about 10 cm and a minor dimension of about 4.0 cm;
a right broad ligament portion, substantially L-shaped, extending from one long edge of the anterior vaginal portion and having a thickness dimension about 1.2 cm and a major dimension of about 3.5 cm;
a left broad ligament portion, substantially L-shaped, extending from another long edge of the anterior vaginal portion and having a thickness dimension about 1.2 cm and a major dimension of about 3.5 cm;
a sacral portion, substantially rectangular in shape, having a major dimension of about 8.0 cm and a minor dimension of about 4.0 cm; and
a posterior vaginal portion, substantially rectangular in shape, having a major dimension of about 15 cm and a minor dimension of about 4.0 cm,
where the left broad ligament portion extends between and connects the anterior vaginal portion and the posterior vaginal portion; and
instructions for implantation of the hysteropexy mesh, said instructions comprising:
creating a peritoneal incision just above a rectum;
separating the rectum from a posterior aspect of a vagina by dissection until a perineal body is reached and levator muscles are exposed;
penetrating a bladder peritoneum overlying a sacral promontory and inferiorly dissecting from a posterior cul de sac;

identifying and clearing off an anterior longitudinal ligament and presacral vessels on the sacral promontory;

manipulating a uterus to create a vesicouterine fascia incision and bladder flap;

dissecting vesicovaginal space to separate a bladder from an anterior aspect of the vagina until a level of a trigone is reached;

creating broad ligament incisions on each side near a cervix;

inserting the hysteropexy mesh and attaching by suture the posterior vaginal portion of the hysteropexy mesh to a posterior aspect of the vagina, passing the anterior vaginal portion of the hysteropexy mesh configured in a folded state and the right and the left broad ligament portions of the hysteropexy mesh through the broad ligament incision on a left;

unfolding the anterior vaginal portion of the hysteropexy mesh and attaching by suture to an anterior aspect of the vagina;

passing the right broad ligament portion of the hysteropexy mesh through the broad ligament incision on a right;

manipulating the uterus and attaching the right broad ligament portion of the hysteropexy mesh to the posterior vaginal portion of the hysteropexy mesh and a posterior aspect of the cervix;

attaching the sacral portion of the hysteropexy mesh to an anterior longitudinal ligament at a level of an S1 vertebrae by suture in a tension free fashion;

closing a peritoneal incision made on a sacrum by suture and cover with the bladder peritoneum using another suture; and closing incisions to complete the method.

* * * * *